(12) United States Patent
Cheal

(10) Patent No.: US 7,803,310 B2
(45) Date of Patent: Sep. 28, 2010

(54) CROSSLINKED POLYETHYLENE ARTICLE

(75) Inventor: Edward J. Cheal, Duxbury, MA (US)

(73) Assignee: OMNI life science, Inc., East Taunton, MA (US)

( * ) Notice: Subject to any disclaimer, the term of this patent is extended or adjusted under 35 U.S.C. 154(b) by 0 days.

(21) Appl. No.: 11/917,603

(22) PCT Filed: Jun. 13, 2006

(86) PCT No.: PCT/US2006/022878

§ 371 (c)(1),
(2), (4) Date: Dec. 14, 2007

(87) PCT Pub. No.: WO2006/138247

PCT Pub. Date: Dec. 28, 2006

(65) Prior Publication Data

US 2008/0197541 A1    Aug. 21, 2008

Related U.S. Application Data

(60) Provisional application No. 60/690,145, filed on Jun. 14, 2005.

(51) Int. Cl.
*B29C 67/00* (2006.01)
(52) U.S. Cl. .................. 264/488; 264/162; 264/235
(58) Field of Classification Search ............... 264/488, 264/162, 235
See application file for complete search history.

(56) References Cited

U.S. PATENT DOCUMENTS

| | | | |
|---|---|---|---|
| 4,600,631 A | 7/1986 | Alei et al. | |
| 4,888,019 A | 12/1989 | Gauneus et al. | |
| 5,030,402 A | 7/1991 | Zachariades | |
| 5,210,130 A | 5/1993 | Howard, Jr. | |
| 5,352,732 A | 10/1994 | Howard | |
| 5,414,049 A | 5/1995 | Sun et al. | |
| 5,422,061 A | 6/1995 | Takahashi et al. | |
| 5,449,745 A | 9/1995 | Sun et al. | |
| 5,543,471 A | 8/1996 | Sun et al. | |
| 5,573,720 A | 11/1996 | Kotzer et al. | |
| 5,577,368 A | 11/1996 | Hamilton et al. | |
| 5,650,485 A | 7/1997 | Sun et al. | |
| 5,684,124 A | 11/1997 | Howard, Jr. et al. | |
| 5,728,748 A * | 3/1998 | Sun et al. ............ 522/65 | |
| 5,753,182 A | 5/1998 | Higgins | |
| 5,824,411 A | 10/1998 | Shalaby et al. | |
| 5,834,113 A | 11/1998 | Shalaby et al. | |
| 5,879,400 A | 3/1999 | Merrill et al. | |
| 6,017,975 A | 1/2000 | Saum et al. | |
| 6,143,232 A | 11/2000 | Rohr | |
| 6,165,220 A * | 12/2000 | McKellop et al. ............ 128/898 | |
| 6,168,626 B1 | 1/2001 | Hyon et al. | |
| 6,174,934 B1 | 1/2001 | Sun et al. | |
| 6,228,900 B1 | 5/2001 | Shen et al. | |
| 6,242,507 B1 | 6/2001 | Saum et al. | |
| 6,245,276 B1 | 6/2001 | McNulty et al. | |
| 6,277,390 B1 | 8/2001 | Schaffner et al. | |
| 6,281,264 B1 | 8/2001 | Salovey et al. | |
| 6,316,158 B1 | 11/2001 | Saum et al. | |
| 6,355,215 B1 | 3/2002 | Poggie et al. | |
| 6,365,089 B1 | 4/2002 | Krebs et al. | |
| 6,372,814 B1 | 4/2002 | Sun et al. | |
| 6,379,741 B1 | 4/2002 | Komvopoulos et al. | |
| 6,395,799 B1 | 5/2002 | Johnson | |
| 6,414,086 B1 | 7/2002 | Wang et al. | |
| 6,432,349 B1 | 8/2002 | Pletcher et al. | |
| 6,436,137 B2 | 8/2002 | Wang et al. | |
| 6,448,315 B1 | 9/2002 | Lidgren et al. | |
| 6,464,926 B1 | 10/2002 | Merrill et al. | |
| 6,494,917 B1 | 12/2002 | McKellop et al. | |
| 6,500,386 B1 | 12/2002 | Burstein | |
| 6,503,439 B1 | 1/2003 | Burstein | |
| 6,547,828 B2 | 4/2003 | Scott et al. | |
| 6,562,540 B2 | 5/2003 | Saum et al. | |
| 6,566,451 B2 | 5/2003 | Wang et al. | |
| 6,627,141 B2 | 9/2003 | McNulty et al. | |
| 6,641,617 B1 | 11/2003 | Merrill et al. | |
| 6,664,308 B2 | 12/2003 | Sun et al. | |
| 6,677,415 B1 | 1/2004 | O'Connor et al. | |
| 6,686,437 B2 | 2/2004 | Buchman et al. | |

(Continued)

FOREIGN PATENT DOCUMENTS

EP    0373800    6/1990

(Continued)

OTHER PUBLICATIONS

International Search Report for PCT/2006/022878, dated Dec. 18, 2006.

(Continued)

*Primary Examiner*—Joseph S Del Sole
*Assistant Examiner*—James Sanders
(74) *Attorney, Agent, or Firm*—Scott E. Kamholz; Peter K. Sollins; Foley Hoag LLP

(57) ABSTRACT

A method of manufacturing an article may include crosslinking a UHMWPE preform, shaping the crosslinked preform, heat-treating the shape in a temperature-controlled oven and low-oxygen environment, and inspecting the heat-treated shape for conformance to article specifications.

26 Claims, No Drawings

U.S. PATENT DOCUMENTS

| | | |
|---|---|---|
| 6,692,679 B1 | 2/2004 | McNulty et al. |
| 6,709,464 B2 | 3/2004 | Scott et al. |
| 6,726,727 B2 | 4/2004 | Scott et al. |
| 6,786,933 B2 | 9/2004 | Merrill et al. |
| 6,790,923 B2 | 9/2004 | Smith et al. |
| 6,794,423 B1 | 9/2004 | Li |
| 6,818,171 B2 | 11/2004 | Wang et al. |
| 6,849,224 B2 | 2/2005 | Wang et al. |
| 2002/0037944 A1* | 3/2002 | Shen et al. .................. 522/153 |
| 2003/0127778 A1* | 7/2003 | Scott et al. .................. 264/485 |
| 2003/0219596 A1* | 11/2003 | Antal et al. .................. 428/373 |
| 2003/0229155 A1 | 12/2003 | Wang et al. |
| 2004/0156879 A1* | 8/2004 | Muratoglu et al. .......... 424/423 |
| 2005/0043431 A1 | 2/2005 | Wang et al. |
| 2005/0113935 A1 | 5/2005 | Wang et al. |

FOREIGN PATENT DOCUMENTS

| | | |
|---|---|---|
| EP | 0446300 | 9/1991 |
| EP | 0722973 | 7/1996 |
| EP | 0729981 | 9/1996 |
| EP | 0722973 B1 | 12/2003 |

OTHER PUBLICATIONS

Written Opinion for PCT/2006/022878, dated Dec. 18, 2006.

* cited by examiner

CROSSLINKED POLYETHYLENE ARTICLE

CROSS-REFERENCE TO RELATED APPLICATIONS

This application is the National Stage of International Application No. PCT/US2006/022878, filed Jun. 13, 2006, which claims the benefit of U.S. Provisional Application No. 60/690,145, filed Jun. 14, 2005, which is hereby incorporated herein by reference.

FIELD

The present invention relates generally to articles, and methods of manufacturing them, that may be particularly suitable for use as components of an artificial joint prosthesis and more particularly to components that act as bearing surfaces, such as the acetabular component of a hip prosthesis.

BACKGROUND

Artificial joint prostheses are widely used today, restoring mobility to patients affected by a variety of conditions, particularly arthritis. The satisfactory performance of these devices can be affected not only by the design of the component itself, but also by the long term wear resistance of the bearing components. Inadequate wear resistance can lead to the generation of harmful debris; continued wear can ultimately lead to component failure due to wear through, fracture, loosening, or dislocation of one or more of the involved implants.

Ultrahigh molecular weight polyethylene (hereinafter referred as "UHMWPE") has proven to be a useful material for orthopaedic implants that function as bearing components in articulating joints. However, UHMWPE wear debris, if present in excess, can result in lysis of the bone tissue that surrounds and supports the implant, which can in turn lead to the need for surgical revision. Many methods of improving the wear resistance of the UHMWPE used in orthopaedic implants have been proposed and implemented with varying degrees of promise for the long-term survival of the reconstructed joints.

One method to improve the wear resistance of UHMWPE is to increase the degree of crosslinking of the polymer using ionizing radiation, such as gamma ray or electron beam irradiation. Ionizing radiation results in the breaking of carbon-carbon and/or carbon-hydrogen bonds, and the formation of free radicals, at the molecular level of the polymer. In the absence of oxygen, these free radicals can form carbon-carbon crosslinks between adjacent molecules, returning to a stable molecular structure. This stabilization process can be accelerated by elevating the temperature of the irradiated UHMPWE, below, near, or above the melt temperature of the UHMWPE. Based on numerous wear studies from multiple laboratories, the wear resistance of UHMWPE generally increases as the degree of crosslinking of the polymer increases.

However, if oxygen is present during or after irradiation, and the free radicals have not been stabilized by annealing or otherwise, the free radicals can result in oxidative chain scission; during oxidative chain scission, oxygen reacts with a free radical, breaking a polymer chain, and generating a new free radical. This process is hereinafter referred to as "oxidation". Oxidation of UHMWPE can be detrimental to the mechanical properties and wear resistance of the material.

The production of medical devices from UHMWPE is generally done by either machining of preforms, such as bars, plates, or rods, or direct compression molding of parts from UHMWPE powder. Machining can also be applied to molded parts to produce the finished geometry. After the parts are formed, and other steps such as cleaning and inspection are performed as appropriate, the parts are packaged; for many devices, such as orthopaedic joint replacement implants, the parts are sterilized after packaging using any of several suitable methods. Such methods include both ionizing irradiation and non-ionizing methods such as ethylene oxide and gas plasma sterilization.

For these reasons, various methods of irradiating and storing the UHMWPE, which may include heat treatment or other stabilization methods, have been developed to increase the crosslink density while minimizing oxidation of the polymer. Some of these methods include application of ionizing radiation to a preform, such as a bar, plate, or rod, and the application of an elevated temperature during and/or after irradiation, but prior to machining the parts from the treated preform. Other methods include packaging the formed implant devices prior to treatment, and then irradiating the packaged devices either as part of, or in addition to, the sterilization process. These irradiated devices may then be heat treated to stabilize the material.

Since, in some of these methods, the heat treatment is performed on finished parts, it must be applied in such a manner that there is negligible risk of dimensional deviations of the finished parts from the part specifications, so that functionality of the finished parts is not compromised. This can be especially important for parts that, in use, connect or otherwise interact with other parts, such as in modular assemblies, where proper function is dependent on the precise fit of the parts together. When irradiation and/or heat treatment is done on packaged parts, such as when irradiation is used for sterilization, the ability to inspect the parts for dimensional specifications or other physical conformance criteria after irradiation and/or after heat treatment is greatly limited. For this reason, both the irradiation and heat treatment of packaged parts must be done such that dimensional changes, such as deformation or shrinkage of the parts, are minimal. This may require limiting the radiation dose to a dose that is less than optimal for wear performance, since UHMWPE can shrink in response to ionizing radiation. To limit part deformation to acceptable levels, post-packaging heat treatment may require using time and temperature profiles with maximum sustained temperatures significantly below the deformation temperature of UHMWPE (below 80° C.), and corresponding heat treatment time periods exceeding 48 hours, to achieve adequate stabilization of the material.

The fabrication of UHMWPE parts by machining can result in residual stresses in the UHMWPE. These residual stresses can result in deformation of the parts after machining. This can lead to some parts deviating from the design specifications some time after machining, even if the parts met the design specifications immediately after machining. Part designs that include thin walls, complex geometries, and/or small geometric tolerances, for example, can be particularly problematic. The relaxation of residual stresses is accelerated by the application of elevated temperatures. However, if the irradiated preforms are heat treated prior to machining of the preforms, it may take longer for the stress relaxation process to complete. For parts that are heat treated after final packaging, machining techniques to minimize residual stresses must be employed, or the ability to produce parts with certain specifications may be limited.

SUMMARY

A UHMWPE component may be so manufactured as to permit direct physical inspection of the component after crosslinking and stabilization, but prior to final packaging.

The crosslinked and stabilized polyethylene component provides a strong and wear resistant implant material that is not susceptible to significant oxidation. The geometry of the manufactured parts can be precisely verified through direct physical inspection of the components following both crosslinking and stabilization of the UHMWPE material.

In an embodiment, a method of manufacturing an article may include crosslinking a UHMWPE preform, shaping the crosslinked preform, heat-treating the shape in a temperature-controlled oven and low-oxygen environment, and inspecting the heat-treated shape for conformance to article specifications.

DETAILED DESCRIPTION

The present disclosure provides methods for manufacturing articles, particularly implantable joint prosthesis components, that permit direct, physical inspection of the articles before final packaging. The inventor has found that heat-treating a shaped article in a low-oxygen environment prior to packing permits direct physical inspection of the article, thereby facilitating detection and culling or remedying of defective articles. The inventor has also found that such heat-treating before packaging permits additional shaping after heating and before packaging, to permit shaping an article to its final geometry.

The present disclosure describes manufacturing processes that are applicable to implantable prostheses such as hip, knee, elbow, shoulder, and spinal prostheses, all of which may include articulating components. The present invention is particularly advantageous in providing a component composed of UHMWPE that is resistant to wear and is not susceptible to significant oxidative degradation.

The invention begins with preforms of UHMWPE. These preforms can be rods, bars, blocks, or similar forms of UHMWPE that have been fabricated using any of the available commercial processes, including compression molding or ram extrusion to consolidate the UHMWPE powder into these solid forms.

The UHMWPE preforms are irradiated using gamma or electron beam radiation. The radiation dose can fall in a broad range of effective doses. Based on published scientific literature, the minimum dose to achieve significant crosslinking of the polymer is about 2.5 megarads (Mrad) or 25 kilograys (kGy). In general, higher radiation doses result in higher degrees of crosslinking, and higher wear resistance as measured in laboratory wear tests, such as pin-on-disk, or hip or knee joint simulators. However, higher radiation doses can also result in decreased mechanical properties, including tensile strength (ultimate and yield) and elongation at break. For some applications, a radiation dose of 25 Mrad or greater may result in mechanical properties that are not adequate. A radiation dose in the range of about 5 to about 10 Mrad, such as about 8 Mrad, will provide a good trade-off between wear resistance and mechanical properties for most applications, and is the range of preferred radiation dose of the present invention.

After irradiation, the UHMWPE parts are formed from the preforms using lathes, mills, or any other machining devices and processes as appropriate for the material and for the shape and surface characteristics of the specific part design. These methods include, but are not limited to, the well-known fabrication techniques currently used in the commercial production of orthopaedic and spinal implants.

After the UHMWPE parts are machined near or to their final size and shape, the parts are heat treated in a temperature controlled oven and oxygen-free, or nearly oxygen free, environment. "Nearly oxygen-free" may refer to 1% oxygen or less, 0.5% oxygen or less, or 0.1% oxygen or less. Examples of such ovens include industrial vacuum and nitrogen ovens for laboratory use or for commercial heat treatment of production parts. In general, the higher the temperature, the shorter the time period necessary to adequately stabilize the irradiated UHMWPE. For the purposes of manufacturing through-put, effective resource utilization, and cost considerations (including the cost of utilities and of consumables such as nitrogen), the heat treatment time should be as short as possible, specifically less than 48 hours. To stay within this time constraint, the temperature must exceed an average of 80° C. for effective stabilization of the material. To avoid risk of excessive deformation of the parts, the temperature should be significantly below the melt temperature of UHMWPE, with a maximum temperature of 100° C.

The combinations of temperature and time parameters of the present invention may be in the ranges: average temperature in the range of about 80 to about 100° C., for a time period of about 18 to about 36 hours (not including warm-up and cool-down periods of typically 1-3 hours each). The preferred heat treatment parameters are: temperature in the range of about 85 to about 90° C., for a time period of about 24 hours (not including warm-up and cool-down periods). For some particular part designs, such as parts with simple geometric shapes and/or large dimensional tolerances, it may be possible to increase the heat treatment temperature and, optionally, reduce the heat treatment time period from these preferred parameters, while avoiding excessive distortion or deformation of the parts.

After heat treatment of the parts is completed, the parts are inspected for conformance to design specifications. Such inspection may include direct measurement using devices such gauges, calipers, coordinate measurement machines, or profilometers, and/or optical measurements such as optical comparators, as appropriate for the particular design. The inspection process may employ sampling rates of less than 100% for one or more of the specifications, following sampling plans established using standard quality assurance methods or otherwise. The parts then proceed in the manufacturing process, which may typically consist of one or more of the steps of cleaning, packaging, and sterilization. If the parts are sterilized, a non-ionizing method is preferred; example non-ionizing sterilization methods include the commercially available processes that employ ethylene oxide or gas plasma.

As a further embodiment of the present invention, additional machining can be performed after heat treatment to bring parts into conformance to design specifications. This may include resurfacing one or more surface features of the part so as to enable precise control over the final surface geometry, while accommodating small changes in the part geometry that may occur before or during heat treatment. This may be particularly beneficial for parts, for example, that have thin walls, complex geometries, and/or tight tolerances on one or more geometric features.

As part of the present invention, the manufacturing process may be designed and controlled so as to avoid or minimize exposure of the UHMWPE to an oxidative environment during the time period that begins with the irradiation and ends at the completion of the heat treatment. The manufacturing process may employ, but is not necessarily limited to, some or all of the following methods: 1) irradiation of the preforms in an oxygen free environment; this may be accomplished by packaging the preforms in a vacuum, inert, or non-ionizing atmosphere, in a barrier package that is resistant to oxygen transfer, and/or by maintaining an oxygen-free or otherwise inert environment in the radiation chamber; 2) storage of the irradiated preforms in an oxygen-free environment, such as the aforementioned packaging or an inert atmosphere chamber; 3) minimizing the time during which the irradiated UHMWPE is exposed to air, such as during the machining of the parts from the preforms; 3) containment of the parts in a non-oxidizing environment during or in-between the various processing steps, for example if the parts must wait between machining stations such as may be required for the machining of complex geometric designs; such an environment may include, but not necessarily be limited to, nitrogen, water, or other inert or non-ionizing atmosphere, and/or a low temperature environment, such as a deep freezer.

In the preferred embodiment of the present invention, the UHMWPE preforms are sealed in barrier packaging with a nitrogen environment prior to irradiation; the preforms remain in this packaging, with the barrier packaging intact, until just prior to the commencement of machining, and; the total elapsed time from when the irradiated preforms are first exposed to room air until the machined parts begin the heat treatment process does not exceed 24 hours. As an extension of this preferred embodiment, parts may be contained in an inert or non-ionizing environment during at least part of this time, such that the total amount of time during which the parts are exposed to room air or equivalent does not exceed 24 hours, even if the total elapsed time (which includes time in an inert atmosphere) does exceed 24 hours.

EXAMPLE

The following example is provided for illustrative purposes and does not serve to limit the scope of the claims.

Manufacture of Acetabular Cup Liners

A compression-molded UHMWPE rod may be exposed to a gamma radiation dose of 8 Mrad. The rod may be stored in gas-impermeable packaging and/or an oxygen-free or near-oxygen free environment (such as a nitrogen environment). The rod may then be machined a first time to form one or more acetabular cup liners that include extra material (such as about 0.02 inches or about 0.5 millimeters of extra material) on an least one surface or on all surfaces. Within 24 hours from removal of the rod from the gas-impermeable packaging and/or low oxygen environment, the liner(s) may be heat-treated. Alternatively, the partially or fully formed liner(s) may be stored in an non-ionizing environment, such that the total time that the irradiated UHMWPE material is exposed to room air or equivalent prior to commencement of heat treatment does not exceed 24 hours. The heat treatment may last, for example, for 24 hours. It may be carried out in an oxygen-free or near-oxygen-free environment. It may provide an average temperature to the liner of about 85 degrees Celsius. After heat treatment, the liner(s) may be machined a second time to remove the extra material and bring the liner(s) to final dimensional specifications. The liner(s) may then be inspected and/or tested for conformance with those specifications and/or with other criteria (such as absence of cracks and/or contaminants, stress testing, etc.). The finished liner(s) may then be packaged. Finally, it may be sterilized, such as by ethylene oxide treatment.

The invention claimed is:

1. A method of manufacturing an article formed at least in part by ultra-high molecular weight polyethylene (UHMWPE), comprising:
   irradiating a UHMWPE preform; then
   machining the article from the preform such that material in excess of a final geometry of the article remains; then
   heat-treating the machined irradiated preform in a low-oxygen or oxygen-free environment, at a temperature below the UHMWPE melt temperature, to form an irradiated, machined, and stabilized article;
   further machining the article to remove the excess material; and then
   inspecting the irradiated, machined, and stabilized article for conformance to article specifications.

2. The method of claim 1, wherein irradiating comprises delivering a radiation dose in the range of about 5 Mrad to about 10 Mrad.

3. The method of claim 2, wherein the radiation dose is about 8 Mrad.

4. The method of claim 1, further comprising maintaining the preform in a low-oxygen or oxygen-free environment during irradiation.

5. The method of claim 1, further comprising storing the irradiated preform prior to machining.

6. The method of claim 5, further comprising maintaining the preform in a low-oxygen or oxygen-free environment during storage.

7. The method of claim 6, further comprising maintaining the preform in a low-oxygen or oxygen-free environment during irradiation.

8. The method of claim 1, further comprising minimizing the amount of time during which the irradiated preform is exposed to air.

9. The method of claim 1, further comprising maintaining the preform or article in a non-oxidizing environment.

10. The method of claim 9, wherein the preform or article is maintained in a non-oxidizing environment during at least one of irradiating, machining, heat-treating, and inspecting.

11. The method of claim 9, wherein the preform or article is maintained in a non-oxidizing environment for at least some of the time period between two consecutive steps.

12. The method of claim 11, wherein the preform or article is maintained in a non-oxidizing environment during at least one of irradiating, machining, heat-treating, and inspecting.

13. The method of claim 1, further comprising completing all steps following irradiation of the preform and just before commencement of heat treatment such that the total exposure time to room air or equivalent is no more than 24 hours.

14. The method of claim 1, further comprising packaging the inspected article.

15. The method of claim 14, further comprising completing all steps following irradiation of the preform and just before commencement of heat treatment such that the total exposure time to room air or equivalent is no more than 24 hours.

16. The method of claim 1, wherein heat-treating has a duration of about 18 hours to about 36 hours.

17. The method of claim 1, wherein the heat-treating has a duration of about 24 hours at an average temperature in the range of about 85 to about 90 degrees Celsius.

18. The method of claim 1, wherein heat-treating is performed in a vacuum oven or a nitrogen oven.

19. A method of manufacturing an article formed at least in part by ultra-high molecular weight polyethylene (UHMWPE), comprising in the following order:
   irradiating a UHMWPE preform; then
   machining the article from the preform such that material in excess of a final geometry of the article remains; then
   heat-treating the article in a low-oxygen or oxygen-free environment at an average temperature in the range of about 80 to about 100 degrees Celsius; then
   further machining the article to remove the excess material; and then
   inspecting the article for conformance to a specification.

20. The method of claim 19, further comprising packaging the article after inspection.

21. The method of claim 19, further comprising storing the preform in a low-oxygen environment at least during the period after irradiating and before machining the article from the preform.

22. The method of claim 19, wherein the excess material comprises a layer of about 0.02 inches on at least one surface of the article.

23. The method of claim 19, wherein heat-treating is performed for up to about 24 hours at a temperature in the range of about 85 to about 90 degrees Celsius.

24. The method of claim 19, wherein the preform is irradiated with about 8 Mrad of gamma radiation.

25. A method of manufacturing an article formed at least in part by ultra-high molecular weight polyethylene (UHMWPE), comprising in the following order:
   irradiating a UHMWPE preform with about 8 Mrad of gamma radiation; then
   machining the article from the preform such that about 0.02 inches of material in excess of a final geometry of the article remains on at least one surface of the article; then
   heat-treating the article in a low-oxygen or oxygen-free environment for up to about 24 hours at a temperature in the range of about 85 to about 90 degrees Celsius; then
   further machining the article to remove the excess material; then
   inspecting the article for conformance to a specification; then
   packaging the article; and then
   sterilizing the article.

26. The method of claim 20, further comprising sterilizing the article after packaging.

* * * * *